United States Patent
Beck et al.

(10) Patent No.: US 9,149,334 B2
(45) Date of Patent: Oct. 6, 2015

(54) LIGHT-BASED METHOD FOR THE ENDOVASCULAR TREATMENT OF PATHOLOGICALLY ALTERED BLOOD VESSELS

(75) Inventors: Tobias Beck, Munich (DE); Richard Meier, Aying (DE)

(73) Assignee: DORNIER MEDTECH LASER GMBH, Wessling (DE)

( * ) Notice: Subject to any disclaimer, the term of this patent is extended or adjusted under 35 U.S.C. 154(b) by 351 days.

(21) Appl. No.: 12/911,613

(22) Filed: Oct. 25, 2010

(65) Prior Publication Data

US 2011/0125140 A1 May 26, 2011

Related U.S. Application Data

(63) Continuation of application No. PCT/EP2009/003027, filed on Apr. 24, 2009.

(60) Provisional application No. 61/047,779, filed on Apr. 25, 2008.

(51) Int. Cl.
*A61N 5/06* (2006.01)
*A61B 18/24* (2006.01)
*A61B 18/22* (2006.01)
*A61B 19/00* (2006.01)

(52) U.S. Cl.
CPC ............... *A61B 18/24* (2013.01); *A61B 18/22* (2013.01); *A61B 19/5225* (2013.01)

(58) Field of Classification Search
CPC ........... A61B 18/24; A61B 2018/2261; A61B 18/22; A61B 2017/00057

USPC .................... 606/2–19; 607/88, 89
See application file for complete search history.

(56) References Cited

U.S. PATENT DOCUMENTS

| | | | |
|---|---|---|---|
| 4,519,390 A | 5/1985 | Horne |
| 4,592,353 A | 6/1986 | Daikuzono |
| 4,693,244 A | 9/1987 | Daikuzono |
| 4,722,337 A | 2/1988 | Losch |
| 4,736,743 A | 4/1988 | Daikuzono |
| 4,781,185 A | 11/1988 | Kauphusman et al. |
| 4,822,997 A | 4/1989 | Fuller |
| 4,907,588 A | 3/1990 | Burston |
| 5,071,222 A | 12/1991 | Laakmann |
| 5,098,427 A | 3/1992 | Hessel |
| 5,112,328 A | 5/1992 | Taboada |

(Continued)

FOREIGN PATENT DOCUMENTS

| | | |
|---|---|---|
| CA | 2066963 | 11/1992 |
| CA | 2093297 | 11/1993 |

(Continued)

OTHER PUBLICATIONS

Abou-Jawde, R. et al. Title: An Overview of Targeted Treatments in Cancer Publ: Clinical Therapeutics vol./Iss: 25(8) pp. 2121-2137 Date: 2003.

(Continued)

*Primary Examiner* — Aaron Roane
(74) *Attorney, Agent, or Firm* — King & Spalding LLP

(57) ABSTRACT

A light-based method of endovascular treatment, in particular, of pathologically altered blood vessels. Provided are a Method of Endovascular Light Treatment and a corresponding Endovascular Light Application Device.

16 Claims, 3 Drawing Sheets

(56) References Cited

U.S. PATENT DOCUMENTS

| | | | |
|---|---|---|---|
| 5,130,533 A | 7/1992 | Ruf | |
| 5,133,035 A | 7/1992 | Hicks | |
| 5,139,494 A | 8/1992 | Freiberg | |
| 5,154,708 A | 10/1992 | Long | |
| 5,300,066 A | 4/1994 | Manoukian | |
| 5,360,447 A | 11/1994 | Koop | |
| 5,409,483 A * | 4/1995 | Campbell et al. | 606/15 |
| 5,409,537 A | 4/1995 | Poullos | |
| 5,415,655 A | 5/1995 | Fuller et al. | |
| 5,416,878 A | 5/1995 | Bruce | |
| 5,454,808 A | 10/1995 | Koop | |
| 5,490,849 A | 2/1996 | Smith | |
| 5,520,681 A | 5/1996 | Fuller | |
| 5,535,399 A | 7/1996 | Blitz | |
| 5,540,676 A | 7/1996 | Freiberg | |
| 5,607,420 A | 3/1997 | Schuman | |
| 5,681,307 A | 10/1997 | McMahan | |
| 5,688,263 A | 11/1997 | Hauptmann | |
| 5,690,611 A * | 11/1997 | Swartz et al. | 604/528 |
| 5,693,043 A | 12/1997 | Kittrell et al. | |
| 5,738,679 A | 4/1998 | Daikuzono | |
| 5,742,718 A | 4/1998 | Harman | |
| 5,782,896 A * | 7/1998 | Chen et al. | 607/88 |
| 5,795,311 A | 8/1998 | Wess | |
| 5,841,562 A | 11/1998 | Rangwala | |
| 5,860,972 A | 1/1999 | Hoang | |
| 5,872,618 A | 2/1999 | Nagayama | |
| 5,908,417 A | 6/1999 | Miller | |
| 5,951,543 A | 9/1999 | Brauer | |
| 5,957,915 A | 9/1999 | Trost | |
| 5,971,755 A | 10/1999 | Liebermann | |
| 6,022,345 A | 2/2000 | Miller | |
| 6,086,366 A | 7/2000 | Mueller | |
| 6,092,722 A | 7/2000 | Heinrichs | |
| 6,143,018 A * | 11/2000 | Beuthan et al. | 607/88 |
| 6,162,218 A | 12/2000 | Elbrecht | |
| 6,193,711 B1 | 2/2001 | Connors | |
| 6,270,491 B1 | 8/2001 | Toth | |
| 6,273,885 B1 | 8/2001 | Koop | |
| 6,377,591 B1 | 4/2002 | Hollister | |
| 6,398,777 B1 * | 6/2002 | Navarro et al. | 606/7 |
| 6,398,778 B1 | 6/2002 | Gu et al. | |
| 6,423,055 B1 | 7/2002 | Farr et al. | |
| 6,477,426 B1 | 11/2002 | Fenn et al. | |
| 6,567,582 B1 | 5/2003 | Rizoiu et al. | |
| 6,699,239 B1 | 3/2004 | Stiller et al. | |
| 6,829,427 B1 | 12/2004 | Becker | |
| 6,986,766 B2 * | 1/2006 | Caldera et al. | 606/15 |
| 7,006,749 B2 | 2/2006 | Illich et al. | |
| 7,020,361 B2 | 3/2006 | Thiele et al. | |
| 7,114,855 B2 | 10/2006 | Wittrisch | |
| 7,215,864 B1 | 5/2007 | Qian et al. | |
| 7,503,701 B2 | 3/2009 | Hiereth et al. | |
| 2002/0073082 A1 | 6/2002 | Duvillier | |
| 2002/0081080 A1 | 6/2002 | Balle-Petersen | |
| 2002/0183811 A1 | 12/2002 | Irwin | |
| 2003/0130649 A1 | 7/2003 | Murray et al. | |
| 2004/0037498 A1 | 2/2004 | Thiele | |
| 2004/0092913 A1* | 5/2004 | Hennings et al. | 606/3 |
| 2004/0114879 A1 | 6/2004 | Hiereth et al. | |
| 2005/0013551 A1 | 1/2005 | Hung | |
| 2005/0038419 A9 * | 2/2005 | Arnold et al. | 606/15 |
| 2005/0105859 A1 | 5/2005 | Gerhard | |
| 2005/0131400 A1* | 6/2005 | Hennings et al. | 606/15 |
| 2006/0122281 A1 | 6/2006 | Escandon et al. | |
| 2006/0217692 A1* | 9/2006 | Neuberger | 606/12 |
| 2007/0179485 A1 | 8/2007 | Yeik et al. | |
| 2007/0219601 A1 | 9/2007 | Neuberger | |
| 2008/0033341 A1 | 2/2008 | Grad | |
| 2008/0071333 A1 | 3/2008 | Hayes et al. | |

FOREIGN PATENT DOCUMENTS

| | | |
|---|---|---|
| DE | 8416748.3 | 8/1984 |
| DE | 9013085.5 | 1/1991 |
| DE | 4013455 | 10/1991 |
| DE | 4025851 | 2/1992 |
| DE | 4216254 | 8/1994 |
| DE | 4229566 | 8/1996 |
| DE | 19534590 | 3/1997 |
| DE | 19629646 | 9/1998 |
| DE | 19729978 | 1/1999 |
| DE | 69229128 | 2/2000 |
| DE | 10009004 | 10/2001 |
| DE | 10106297 | 1/2002 |
| EP | 0325836 | 8/1989 |
| EP | 404968 | 1/1991 |
| EP | 433464 | 6/1991 |
| EP | 473987 | 3/1992 |
| EP | 0495605 | 7/1992 |
| EP | 514258 | 11/1992 |
| EP | 0292622 | 12/1996 |
| EP | 0820787 | 1/1998 |
| EP | 1527748 | 5/2005 |
| JP | 03033808 | 2/1991 |
| JP | 2002162524 | 6/2002 |
| WO | WO 93/21841 | 11/1993 |
| WO | WO 98/47032 | 10/1998 |
| WO | WO 99/15237 | 4/1999 |
| WO | WO 04/000099 | 12/2003 |
| WO | WO 2004/012805 | 2/2004 |
| WO | WO 2007/104836 | 9/2007 |

OTHER PUBLICATIONS

Bronchud, M. et al. Title: Selecting the Right Targets for Cancer Therapy Publ: Principles of Molecular Oncology pp. 3-27 Date: 2000.

D'Amico, A. Title: Radiation and Hormonal Therapy for Locally Advanced and Clinically Localized Prostate Cancer Publ: Urology vol./Iss: 58 (Suppl. 2A) pp. 78-82 Date: 2001.

Douwes, F. et al. Title: Neoadjuvant Hormone Ablation before HIFU Treatment of Localized Prostate Cancer Publ: Alternative and Complementary Therapies vol./Iss: 18 (Suppl. 1) pp. A43 Date: Nov. 2004.

Hua, L. et al. Title: High Intensity Focused Ultrasound Combined with Endocrine Therapy in Treating Prostate Cancer Publ: National Journal of Andrology vol./Iss: 11(3) pp. Abstract Date: Mar. 2005.

Hurwitz, M. et al. Title: Feasibility and Patient Tolerance of a Novel Transrectal Ultrasound Hyperthermia System for Treatment of Prostate Cancer Publ: International Journal of Hyperthermia vol./Iss: 17(1) pp. 31-37 Date: 2001.

Lein, M. et al. Title: Laser-Induced Hyperthermia in Rat Prostate Cancer: Role of Site of Tumor Implantation Publ: Urology vol./Iss: 56 pp. 167-172 Date: 2000.

Marberger, M. et al. Title: Energy-Based Ablative Therapy of Prostate Cancer: High Intensity Focused Ultrasound and Cryoablation Publ: Current Opinion in Urology vol./Iss: 17 pp. 194-199 Date: 2007.

Strohmaier, W. et al. Title: Influence of Transrectal Hyperthermia on Prostate-Specific Antigen in Prostatic Cancer and Benign Prostatic Hyperplasia Publ: Urologia Internationalis vol./Iss: 51(I) abstract pp. 28-31 Date: 1993.

Thueroff, S. et al. Title: Neoadjuvant Hormone Ablation before HIFU Treatment of Localized Prostate Cancer Publ: Journal of Endourology vol./Iss: 18(Suppl 1) pp. A43 Date: Nov. 2004.

Trachtenberg, J. et al. Title: Microwave Thermoablation for Localized Prostate Cancer after Failed Radiation Therapy: Role of Neoadjuvant Hormonal Therapy Publ: Molecular Urology vol./Iss: 3(3) pp. 247-251 Date: 1999.

International Search Report for PCT/EP2009/003027 dated Oct. 29, 2009.

* cited by examiner

Principle A

Step 1 guide wire

Step 2

Principle B

LIGHT-BASED METHOD FOR THE ENDOVASCULAR TREATMENT OF PATHOLOGICALLY ALTERED BLOOD VESSELS

RELATED APPLICATIONS

This patent application is a continuation of and claims priority to PCT Patent Application No. PCT/EP2009/003027, entitled "Light-Based Method for the Endovascular Treatment of Pathologically Altered Blood Vessels," filed Apr. 24, 2009, which claims priority to U.S. Provisional Patent Application No. 61/047,779 filed Apr. 25, 2008. The complete disclosure of each of the above-identified priority applications is hereby fully incorporated herein by reference.

The following presents a new, light-based method of endovascular treatment, in particular of pathologically altered blood vessels. Provided are a Method of Endovascular Light Treatment and a corresponding Endovascular Light Application Device.

INTRODUCTION

All sorts of different therapy options are available to the therapist for the treatment of pathologically altered blood vessels. In addition to the classic surgical methods, endovascular therapies have become increasingly important in recent times. In particular, light-based endovascular thermal methods for the obliteration of, for example, insufficient truncal veins have been integrated into the broad spectrum of therapy options for a few years. One of these light-based thermal therapies is Endovascular Laser Therapy (ELT). In this, certain light application systems are placed in the blood vessel which emit therapy light onto the wall of the blood vessel. The therapy light is absorbed by the tissue and/or blood, which causes the vein wall to heat up, leading in turn initially to a thermal necrosis of the cells in the blood vessel wall with a collagen contraction and wall thickening, usually followed by a thrombotic closure of the treated vein. The subsequent inflammatory reaction and repair processes lead, sometimes not before after a number of weeks, to the obliteration of the truncal vein that has been treated and thus to the hemodynamic disconnection of the treated vein segment and branch varicose veins that were supplied by this.

STATE OF THE ART

The aim of endovascular therapy is inter alia to close pathologically altered blood vessels using a minimally invasive method. A procedure currently known and practiced to achieve this therapeutic aim is as follows: After puncturing the vessel to be treated, a simple fiberglass or complex-structure energy applicator or light applicator is positioned intravenously usually via a type of catheter system using a sort of Seldinger technique and therapeutic light is applied in this way. Before or during the treatment, however, the catheter system, which is only used for positioning, is generally pulled out of the vessel along with the light applicator, whilst emitting the laser light. It is assumed that the blood vessel closes immediately with this treatment method, especially because of the instant contraction and/or the formation of a thrombus. With this method, the light is usually applied to a limited area of the vessel during a short period of time.

These systems of the prior art, especially within ELT, often suffer from high local temperatures of several 100° C. up to more than 1000° C. This leads to a variety of problems, including protein agglomeration or aggregation, carbonizing of organic material or unwanted destruction or perforation of healthy structures or ingredients of body fluid or even of the applicator. This may lead to clinical complications such as hematomas, phlebitis, erythema, ecchymosis and other lesions of tissues, e.g. also at nerves, or even unspecific pain.

When applying the Seldinger Technique, the desired vessel or cavity is punctured with a sharp hollow needle, also called access needle or trocar, optionally with ultrasound guidance if necessary. Commonly a round-tipped guidewire is then advanced through the lumen of the access needle, and the access needle is withdrawn. The catheter or "catheter sheath" is inserted along the guidewire into the cavity or vessel, optionally after enlarging the puncture channel employing a dilator. After final introduction of the catheter sheath, the guidewire is withdrawn.

Ultrasound guidance or fluoroscopy may be used to confirm the position of the catheter and to manoeuvre it to the desired location. Injection of radiocontrast may be used to visualise organs. Interventional procedures, such as thermoablation, angioplasty, embolisation or biopsy, may be performed.

Upon completion of the desired procedure, the sheath is withdrawn. In certain settings, a sealing device may be used to close the hole made by the procedure.

In the prior art the light emitting part of the light applicator, usually a special fibre tip or especially a bare fibre tip, is always shifted through the open distal end of the catheter (catheter sheath) and is used in contact with the vessel and/or fluid within the vessel withdrawing applicator and catheter (catheter sheath) together while applying light.

Other approaches of the prior art directly introduce the light applicator only into the vessel. This is an one step technique. Upon percutaneous puncture of the vessel, the light applicator is introduced into the vessel and moved to the location of interest within the vessel, often with ultrasound guidance and while the light applicator is moved back (in direct contact with the vessel or fluid within the vessel) light energy is applied to the length of the vessel that shall be treated. A repeated moving of the light applicator to the same position is impossible. A punctual adhesion of tissue or blood on the surface of the applicator may even lead to a local overheating of the vessel or the applicator.

WO99/12489, U.S. Pat. No. 7,396,355, U.S. Pat. No. 6,752,803 and U.S. Pat. No. 6,258,084 disclose an electrocatheter suitable for shrinking blood vessels upon applying energy. The catheter comprises working electrodes, which are—when used—expanded from the catheter and are in direct contact with the blood vessel to be treated. In use, a tumescent fluid is injected into the tissue surrounding the treatment site. A further development of this electrocatheter is disclosed in WO 00/10475, U.S. Pat. No. 6,769,433 and U.S. Pat. No. 7,406,970. The electrode is put in apposition with the vessel wall and the wall is pre-shaped before applying energy to the electrodes.

WO 2007/014063 discloses a catheter including a therapeutic element, such as a resistive heating element usable to deliver energy for ligating, or reducing the diameter of a vessel.

US20060069417 discloses a catheter, which introduces electrodes in a vein for a minimally invasive treatment of venous insufficiency by the application of energy to cause selective heating of the vein. The catheter is positioned within the vein to be treated, and the electrodes on the catheter are moved toward one side of the vein. RF energy is applied in a directional manner from the electrodes at the working end of the catheter to cause localized heating and corresponding shrinkage of the adjacent venous tissue.

WO00/44296 and EP 1156751 B1 disclose an endovascular laser device for treating varicose veins. The device of EP 1156751 B1 comprises a
  a) laser of a wavelength in the range 500-1100 nm, which delivers laser energy in bursts and is arranged to emit laser energy to cause thermal damage to a vein wall so as to result in a subsequent decrease in the diameter of said vein;
  b) a fibre optic line; and
  c) an angiocatheter for insertion into a blood vessel,
wherein said angiocatheter and said fibre optic line are arranged and adapted such that in use said fibre optic line makes intraluminal contact with a vein wall and said fibre optic line ends in a bare tip and the tip of said fibre optic line is arranged and adapted to be in direct contact with said vein wall during treatment of said vein.

However, similar to the other catheters of the prior art, in which energy is applied upon contacting an energy or light applicator to the interior wall of the vessel, this device of EP 1156751 B1 may cause unwanted damage to the interior wall of the vessel to be treated due to the exposure of the fibre optic line to the vessel wall. In addition, when in use the free fibre optic line of EP 1156751 B1 may cause pain and small injuries such as perforations and hematomas. Moreover, there is a risk that the fibre optic line breaks during treatment and may be lost, at least partially, in the vessel.

Thus, there is a need in the art to provide an improved device for intraluminal treatment of blood vessels, which allows a safer treatment of patients, reduces risks and pain and preferably allows a better controlled application of light energy to the blood vessels.

SUMMARY OF THE INVENTION

To fulfill this need, the present invention provides a blood vessel treatment device comprising: a light applicator connected to the light emitting unit, and a catheter/applicator tube for inserting the light applicator into and for guiding the light applicator within a vessel, wherein said catheter and said light applicator are arranged and adapted such that in use at any time said light applicator does not make intraluminal contact with any vessel wall and the light applicator is capable of delivering light energy through the sheath of the catheter so as to emit light energy to cause damage to a vessel wall, preferably so as to result in a subsequent decrease in the diameter of said vessel.

This device surprisingly overcomes the problems in the art arising from applying high energy densities while contacting the light applicator directly to the vessel, such as high local temperatures, protein agglomeration or aggregation, carbonizing of organic material or unwanted destruction of healthy structures or ingredients of body fluid or the applicator itself. Surprisingly, although the catheter is not removed until the application of energy to the vessel has been completed (i.e. the catheter is still in place while the applicator has already been removed), the vessel—upon removal of the catheter— shrinks or collapses as intended.

With this surprising solution, also vessels may be treated safely, which encompass many bendings or vessels at bends or at constrictions may be treated, since the catheter protects the vessel from the risk of local damage arising from contact with the light applicator. Also a punctual adhesion of tissue or blood on the surface of the applicator is methodically and technically excluded, inhibiting local overheating of the vessel or the applicator.

Even if the light applicator should be damaged, the catheter protects the vessel from damage. In case of break-down, the fragments of the light applicator can be easily withdrawn from the vessel, since they remain inside the catheter.

The skilled person may easily control and/or optimize the result of the treatment. In a preferred embodiment, thus, an ultrasound or radioactive imaging unit for imaging the treated vessel and/or a temperature or coagulation detecting unit are placed within the catheter.

The device is preferably a sterile device. Sterilization and reuse of the applicator is comparatively easy, since the light applicator is not in contact with body fluids, tissue or the vessel to be treated.

Two embodiments of the device are particularly preferred. In the first embodiment, the device is open at the distal end and the catheter may be introduced into the vessel employing the Seldinger Technique. In the second embodiment, the device is closed at the distal end and the catheter may be introduced into the vessel in a one-step-process, without the need of using a wire guide. Both embodiments are described in detail below and are exemplarily shown in FIG. 2.

The devices of these two embodiments may even be compatible with each other, i.e. the device of the present invention may such that it can be inserted employing both techniques. Accordingly, in a third embodiment—for the first time to our knowledge with the same device—a change between these two techniques even during the therapeutic intervention is possible; just the catheter has to be changed or only to be modified, e.g. cut, at the tip.

In addition, a kit is provided comprising one or more light applicators, e.g. for different purposes or different laser units; a catheter for inserting the light applicator into and for guiding the light applicator within a vessel; a guide wire; and an access needle, wherein said catheter and said light applicator are arranged and adapted such that in use at any time said light applicator does not make intraluminal contact with any vessel wall and the light applicator is capable of delivering light energy through the sheath of the catheter so as to emit light energy to cause damage to a vessel wall, preferably so as to result in a subsequent decrease in the diameter of said vessel.

Also provided is a method of applying light energy from a light emitting unit to a blood vessel, from within the vessel, the method comprising the steps of: introducing into the vessel the device as described above; and applying energy to the vessel until the vessel is damaged, preferably until the damage results in a decrease in the diameter of said vessel; further provided is a method of damaging a vessel using light energy from a light emitting unit, the method comprising the steps of: introducing into the vessel the device as described above; and applying energy to the vessel until the vessel is damaged, preferably until the damage results in a decrease in the diameter of said vessel.

In analogy to the embodiments of the device of the present invention, also the method of the present invention is represented by two preferred embodiments. In the first embodiment, the device is open at the distal end and is introduced into the vessel employing the Seldinger Technique or kind of Seldinger Technique. In the second embodiment, the device is closed at the distal end and the catheter may be introduced into the vessel in a one-step-process, without the need of a wire guide.

All these methods allow for cosmetic treatment of varicose veins or alternatively the treatment of pathologically altered blood vessels for medical purposes.

However, with this new method, the light applicator is guided in the catheter system for the duration of the therapy (e.g. with a speed of approx. 1-5 mm/s) and the catheter itself is only pulled out of the vessel after completion of the light treatment, preferably until after the damaging of the vessel wall treated by (laser) light is achieved. Because the light applicator is guided in the catheter system, there is no direct contact between the light applicator and the blood vessel wall (see illustration in FIG. 1). In addition, with this measure, the vessel or vein to be closed is prevented, during the entire laser application by a sort of catheter system, from shrinking immediately or completely closing. This catheter system is therefore also a central component of a suitable blood vessel treatment device or light application system and light is passed through it during the continuous or a section-wise treatment. The catheter itself may also redefine or further optimize the desired light emission properties of the light applicator. The blood vessel is largely kept open for the duration of the therapy, and the immediate closure of the vessel is prevented. The treated blood vessel may only be obliterated after treatment when the catheter system is removed.

DETAILED DESCRIPTION OF THE INVENTION

In one aspect, the present invention provides a vessel treatment device comprising: a light applicator connected to the light emitting unit; and a catheter for inserting the light applicator into and for guiding the light applicator within a vessel, wherein said catheter and said light applicator are arranged and adapted such that in use at any time said light applicator does not make intraluminal contact with any vessel wall and the light applicator is capable of delivering light energy through the sheath of the catheter so as to emit light energy to cause damage to a vessel wall, preferably so as to result in a subsequent decrease in the diameter of said vessel.

The device is suitable to treat any hollow vessel in a mammal, preferably in a human.

The "vessel" may be any hollow anatomical structure. In a preferred embodiment, the vessel is a blood vessel, most preferably a vein.

Conditions of said vessel to be treated in line with the present invention encompass the treatment of varicose veins for cosmetic and/or therapeutic purposes and, optionally, in connection with a tumescence local anesthesia. Also in line with the present invention is a single or multiple treatment of a vessel by photodynamic therapy.

Preferably, the vessel treatment device further comprises a light emitting unit, said light emitting unit being connected to the light applicator. The light may be laser light. The light emitting unit may be a laser, e.g. a pulsed laser or CW laser, or another means for inducing a thermal effect and/or a photodynamic effect. Any conventional or commercially available laser may be employed.

In many embodiments of the present invention, the wavelength of the laser light or emitted by the laser is in the range of about 500-2000 nm referring to the optical properties of tissue, preferably in the range of 700-1500 nm.

The Power of the light emitting unit, e.g. of the laser, may be in the range of 1 to 150 W, preferably in the range of 10 to 50 W, more preferably 15 to 40 W.

The Energy and the power density applied per $cm^2$ at the emitting surface or emitting area of the light applicator is much lower (at least 1 to 3 magnitudes lower) than in conventional applicators, since the energy emitting part ("emitting surface" or "emitting area") of the applicator is much larger than in the prior art, where only a bare fiber or other locally very confined tip area emits light. According to the invention the length of emitting surface or emitting area is preferably in the range of 3 to 70 mm, more preferably in the range of 10 to 30 mm. In a preferred example the emitting part is about 25 mm long. The area of the emitting surface or emitting area of the light applicator is in the range of 0.1 $cm^2$ to 10 $cm^2$, preferably 0.5 $cm^2$ to 5 $cm^2$, most preferably 1 $cm^2$ to 3 $cm^2$. The power density at the emitting surface or emitting area of the light applicator is in the range of 1 to 200 $W/cm^2$, preferably 10 to 100 $W/cm^2$, and most preferably 20 to 35 $W/cm^2$.

Also the radiation profile and the easy movability of the light applicator may be adapted to allow to overcome the disadvantages of the point-shaped energy application of the prior art, e.g. protein carbonization. The overall energy needed can be better controlled employing the movable light applicator and/or the radiation profile of the present invention.

The light applicator is connectable to the light emitting unit. In one embodiment, the light applicator is a fibre optic line, preferably comprising a light applicator tip or a fibre optic tip, most preferably a cylindrical diffuser.

The light applicator may have a length of e.g. 10 to 500 cm, preferably 30-300 cm, more preferably, 200-300 cm. This applies in particular, if the light applicator is a fibre optic line.

The diameter of the light applicator may e.g. be between 0.1 and 2.5 mm, preferably in the range of 0.3 to 1.9 mm, more preferably in the range of 0.5 to 1.8 mm, even more preferably in the range of 0.7 to 1.7 mm, even more preferably in the range of 1.0-1.6, most preferably in the range of 1.1 to 1.2 mm. This applies in particular, if the light applicator is a fibre optic line. The diameter of the catheter is always a bit (approximately 0.1 to 2 mm) bigger than of the corresponding light applicator. A catheter, which is inserted using the Seldinger Technique, is normally of a larger diameter compared to a catheter inserted in a one step procedure.

In one embodiment, the diameter of the fibre optic tip is between 0.1 and 2.5 mm, preferably in the range of 0.6 to 2.4 mm, more preferably in the range of 1.0-2.3 mm; even more preferably in the range of 1.3 to 2.2 mm, even more preferably in the range of 1.4 to 2.1 mm; even most preferably in the range of 1.5-1.9 mm.

The light applicator may be of a uniform cylindrical shape. In one embodiment, the light applicator emits light in a cylindrical, ideally radial profile.

In one embodiment, the light applicator comprises light emitting areas, which are locally or systemically distributed in front of the fibre surface and are capable of emitting light more or less perpendicular to the fibre axis. Preferably, the light emitting areas are placed at the distal end of the light applicator and extend over 1 to 10 cm, preferably 2 to 5 cm. The light emitting areas may comprise scattering particles.

FIG. 3 shows a homogeneous and an inhomogeneous cylindrical radiation profile.

The homogeneous cylindrical radiation profile preferably has a length along the axis of 1 to 5 cm, more preferably 2 to 4 cm, most preferably 2 to 3 cm. This leads to a reduced light intensity, as compared to the prior art, which conventionally employs a non-areal, but point-shaped light emission by a optic fibre laser tip, thereby applying very high local intensities.

In particular embodiments, an inhomogeneous distribution may be reasonable to further reduce the total necessary light energy. At the proximal end of the emitting area more light is applied as at the distal end. This mode of emitting light, causing fast preheating of the tissue at the proximal end, saves energy since the total energy required is somewhat lower when compared to homogenous profile, as e.g. shown in FIG. 3a. The exact shape of the preferred embodiment is a kind of exponential decay, as this can be easily realized by volume scattering. Also the inhomogeneous cylindrical radiation profile preferably has a length along the axis of 1 to 5 cm, more preferably 2 to 4 cm, most preferably 2 to 3 cm.

The catheter is for inserting the light applicator into the vessel and for guiding the light applicator within the vessel. In general, any conventional catheter may be employed, as long as this catheter is highly transparent for the therapeutic light and inter alia photochemically inert. In preferred embodiments, it is made of Teflon or PTFE. Wherever reference is made to a "catheter", this is meant to encompass also any applicator tube in general.

Preferably, the catheter, in particular the sheath of the catheter, i.e. its tubular envelop, is partially, more preferably fully optically transmissible for light emitted from the light applicator. The surface of the catheter or the sheath of the catheter may have a coating, e.g. a hydrophilic coating. A hydrophilic coating allows for easier inset into and removing out of the blood vessel. Preferably, the distal end of the catheter is closed. More preferably, also the sheath of the catheter is cylindrical and fully optically transmissible for light emitted from the light applicator. The sheath of the catheter may even help, e.g. to homogenize, the radiation profile.

Catheter and light applicator are arranged and adapted such that in use at any time said light applicator does not make intraluminal contact with any vessel wall. Preferably the light applicator is placed within the sheath of the catheter, and may be flushed, preferably by a transparent physiological solution. Here, the catheter may be open to or in open contact with the fluid within the vessel, although the light applicator does not protrude from the catheter or the catheter sheath and stays safely secured inside the catheter.

If the catheter is open, the device may be introduced employing the Seldinger Techniques, i.e. using a guide wire in analogy to classical insertion processes of the prior art as explained above. However, in this invention, the light applicator is not shifted through the open distal end of the catheter so that the light applicator does not make intraluminal contact with the vessel, i.e. the applicator does not make intraluminal contact with any vessel wall (see also FIG. 2, "principle A"). The catheter in this embodiment is flushable and flushing fluid, preferably an aqueous solution, more preferably a physiological solution may be used to clean and/or cool the light applicator.

If the catheter is closed, the device may be introduced employing a one step technique, i.e. without using a guide wire. After puncture of the vessel, the catheter is inserted into the vessel (see also FIG. 2, "principle B"). This is contrary to the prior art, wherein only the light applicator is introduced in such a one step technique, but not a catheter bearing the light applicator. The catheter may or may not encompass the light applicator during the insertion step depending on the rigidity of the device encompassing catheter and light applicator needed. The catheter alone is more flexible, while catheter together with light applicator is a more rigid unit.

In preferred embodiments, the light applicator is intended not to be in contact with blood when in use. These embodiments minimize the risk to create carbonization effects in the vessel, since neither vessel, nor blood are in contact with the light applicator and there is no primary heat of the light applicator as energy is transferred by the emitted light. Also secondary heat within the applicator can be attenuated given by the spacing between light applicator inside the catheter and the (part of the) vessel to be treated.

The minimal distance from the light applicator tip to the distal end of the catheter is in the range of 1.0 to 30 mm, preferably in the range of 2.0 to 20 mm, more preferably in the range of 3.0 to 10 mm, most preferably in the range of 5.0 to 8.0 mm.

The light applicator is capable of delivering light energy through the sheath of the catheter and to cause damage to a vessel wall. This delivering of light energy preferably results in a subsequent decrease in the diameter of said vessel wall; most preferably until the shrinkage or collapse of vessel wall.

The light applicator during use may be placed repeatedly at the same position within the vessel with or without moving the catheter. Preferably, the light applicator is movable within the catheter; more preferably the light applicator is movable within the catheter when in use. Most preferably the light applicator is movable with constant velocity, e.g. with a velocity of 1 to 5 mm/s, preferably 1.0 to 4.0 mm/s, more preferably 2.0 to 3.0 mm/s; most preferably, the velocity is controlled by a velocity control unit.

It is also conceivable that the catheter and light applicator are moved towards each other at different speeds.

Visible pilot light, coupled into the applicator, could also be used, for example, to determine the position of the light applicator. Other types of labels may be used alternatively, e.g. fluorescent markers.

In a preferred embodiment, the blood vessel treatment device of the invention further comprises an ultrasound, magnetic resonance or radioactive imaging unit for imaging the vessel to be treated; and/or a velocity control unit for controlling the velocity with which the light applicator is moved within the catheter and/or a temperature or coagulation detecting unit inside the catheter for determining the temperature or tissue properties at the position, where the vessel is damaged and/or an imaging unit, connected to the one or more of the three units above for displaying the data measured by these one or more units. In addition a closed loop unit may be present based on the imaging unit, which closed loop unit provides a feedback controlling the parameters light intensity and/or velocity or segmentation of movement. "Segmentation of movement" means that the light applicator is moved stepwise, i.e. moved to one position in the catheter, keep for a short time interval and moved to a next position, and so on.

The temperature when using the device of the present invention is preferably kept in the range between 37° C. and 200° C., more preferably below 150° C., most preferably below 100° C. Each position is preferably "heated" by employing the light applicator for 1 to 25 s, more preferably 2 to 15 s, most preferably 5 to 10 s. This time range helps to allow a mild treatment, thereby avoiding high temperatures. If more energy needs to be applied to a particular position in order to deliberately damage or shrink the vessel, the light applicator can be moved and used several times to treat the same position.

In its second aspect, the present invention provides a kit comprising one or more light applicators; a catheter for inserting light applicator into and for guiding the light applicator within a vessel; a guide wire; and an access needle, wherein said catheter and said light applicator are arranged and adapted such that in use at any time said light applicator does not make intraluminal contact with any vessel wall and the light applicator is capable of delivering light energy through the sheath of the catheter so as to emit light energy to cause damage to a vessel wall, preferably so as to result in a subsequent decrease in the diameter of said vein wall. The kit may be used to prepare the device of the first aspect of the present invention and to insert said device employing the Seldinger Technique.

In its third aspect, the present invention provides a method of applying light energy from a light emitting unit to a vessel from within the vessel, the method comprising the steps of: introducing into the vessel the device of the first aspect of the invention and applying energy to the vessel until the vessel is damaged or collapses. While the light emitting unit may be introduced into the vessel, e.g. in a miniaturized version, it is preferred herein that "introducing into the vessel the device of the first aspect of the invention" means that only the catheter and the light applicator are introduced into the vessel and the light emitting unit, if part of the device, is connected thereto, but stays outside the vessel.

"Collapse" or "collapse of the vessel" in particular means that the structure of the vessel, in particular of the wall of the vessel is destroyed, preferably so as to close the vessel from any flood of fluid, preferably from flood of blood.

"Damage" or "damage of the vessel" preferably means that the structure of the vessel, in particular of the wall of the vessel is altered in its geometry and/or stability. Preferably, the diameter of the vessel decreases when damage of the vessel occurs. In one embodiment, the vessel decreases in its diameter to less than 90% of the original diameter, i.e. before start of applying energy, preferably, the vessel decreases in its diameter to less than 85%, to less than 80%, to less than 75%, to less than 70%, to less than 65%, to less than 60%, to less than 55%, to less than 50%, to less than 45%, to less than 40%, to less than 35%, to less than 30%, to less than 25%, to less than 20%, to less than 15%, to less than 10%, to less than 5%, to less than 4%, to less than 3%, to less than 2%, to less than 1% of the diameter before applying the light energy, most preferably it shrinks until the vessel is closed or until no fluid or blood can flow through at the damaged position ("obliteration").

Optionally, perivenous tumescence may be used to support the treatment, preferably by administering local anesthesia and/or for reducing the risk of damaging of surrounding tissues, in particular nerve tissues.

Upon finalizing the vessel treatment, shrinkage or damaging, the catheter is withdrawn from the vessel. This may be guided with optical, radioactive or acoustic labels, preferably placed at the distal end of the catheter.

The method of this third aspect of the invention may also be used for damaging a vessel using light energy from a light emitting unit.

In one embodiment, the method of this third aspect of the invention, further comprises the step of placing the light applicator repeatedly, i.e. at least twice, at the same position in the catheter and therewith in the vessel while continuing to apply energy to the vessel. This may allow for a safer and more regular treatment of the vessel. Preferably, the method comprises the step of moving the light applicator in the catheter and therewith in the vessel while continuing to apply energy to the vessel.

In many embodiments, the method of this third aspect of the invention comprises imaging the vessel to be treated, controlling the velocity with which the light applicator is moved within the catheter, or determining the temperature or tissue properties at the position, where the vessel is damaged.

APPLICATIONS OF THE PRESENT INVENTION

In particular, the device and method of the present invention can be used in the treatment of varicose veins and, in particular, in connection with a tumescence local anesthesia.

In the treatment of varicose veins, the shrinking and/or closure of the vein is brought about by a combination of spontaneous contraction, thrombotic closure (on a comparatively small scale) and later fibrotic transformation of the blood vessel and support by secondary effects (such as wound healing). These biological effects are primarily induced through the effect of heat. The absorption of light which causes warming occurs here both in the blood and on the vein wall itself.

The embodiments of the present invention as set forth above, offer the advantages over other techniques in the art in clinical use as follows:

The application system can be introduced into the blood vessel using the Seldinger technique or a modification of the Seldinger technique or directly by using a closed catheter.

During the introduction of the system by Seldinger technique and application of light, the application system can be rinsed via the catheter, e.g. to allow cooling.

During the treatment, the blood vessel wall can be irradiated in several sections, i.e. after a section has been irradiated, the application system is steadily moved forward by roughly the length of this section. It is also conceivable that the outer catheter and inner application parts are moved towards each other at different speeds. Visible pilot light, coupled into the applicator, could also be used, for example, to determine the position of the light applicator.

The closure of the blood vessel after the light treatment presented here can be supported by additional secondary measures such as compression.

In addition to thermal laser applications, this method can also be used for photodynamic applications.

There is almost no risk of unwanted damaging of the vessel to be treated especially due to comparatively extremely low light power densities used, the avoidance of contact and the constant friction between applicator to be moved and catheter without be changed during the application of energy

FURTHER EMBODIMENTS

Ideally, the light in the method described here is emitted on a circular basis and preferably over a particular length. This ensures a more even treatment of the blood vessel. In addition, a cylindrical irradiation over a length of approx. 0.5-5 cm can sensibly balance out lack of homogeneity in the vessel wall and/or irregularities caused by movement of the applicator.

In addition, this applicator may have a higher level of light emission at the proximal end of its irradiation area. This causes a higher level of energy to be given off at the proximal end of the irradiation area when the light applicator is withdrawn than at the distal end. This means that, when the proximal end passes by, the blood vessel wall section being passed by the light applicator quickly heats up from body temperature (approx. 37° C.) to treatment temperature (approx. 60-100° C.). When the distal applicator end passes by, the temperature of the blood vessel wall is not increased dramatically any further, but simply remains constant. This rapid preheating can increase the efficiency of the method as a whole (by minimizing the transport of heat and by changing the optical parameters during preheating).

Suitable wavelengths for the therapy light used in this method are in the visible to infrared range, especially because of the optical absorption and dispersion in the tissue between 500-2000 nm.

The method can be optimized on the basis of an online temperature or tissue properties or geometrical measurement during irradiation or in breaks between irradiation in or on the surface of the application system, or even supported by regulating technology.

Advantages of the New Therapy Method Described Here

The low-friction, even sliding of the light applicator in a type of catheter system during treatment makes it easier for the user to achieve an even treatment result.

Because the catheter remains in the blood vessel during treatment, a defined positioning (minimum distance/centering) of the light applicator is ensured, especially at bends.

With this method, it is possible to treat certain sections of the vessel or the blood vessel over the entire length to be treated several times over. This means that it is possible to achieve closure gently, through several applications of low doses of light or—if therapy monitoring through parallel diagnostic methods is possible—to optimize the treatment result during the intervention.

There is almost no possibility of creating primary thromboses. In particular, with this method, it is not possible to create a carbonized coagulation of blood on the light applicator itself, which could cause indirect thermal damage or even perforation of the blood vessel wall.

Because, with this method, the light-emitting area of the applicator is not in direct contact with the blood, the treatment is more even over the entire length of the blood vessel. The light-emitting area is not changed through any adhesion of blood and/or tissue to the outside of the application system for the entire duration of the treatment.

With this method, the catheter, which remains in the vessel until the treatment is finished, represents an additional safety factor for the method. If any incident occurs, such as damage to the applicator at its light-emitting area, the entire system can be retrieved without parts being left in the body of the patient.

DESCRIPTION OF THE FIGURES

FIG. 2 also shows the introduction of the device of the present invention using a one step process ("principle b"). The catheter itself is used as "guide wire" upon puncture with an access needle and guides the light applicator through the vessel. Here, both are inserted simultaneously. However, in accordance with the present invention, the light applicator may also be inserted subsequently to the insertion of the catheter. Upon positioning the catheter, the light applicator is used to apply energy. The light applicator is movable within the catheter and is capable of emitting light through the catheter, e.g. through the closed distal end and/or especially through the sheath of the catheter in a cylindrical manner. Upon finalizing the treatment, the light applicator may be removed from the catheter. Finally, the catheter is removed from the vessel.

Inserting the catheter with or without the light applicator may depend upon the rigidity needed. The catheter alone is more flexible, while catheter together with light applicator forms a more rigid unit.

Figure 1:
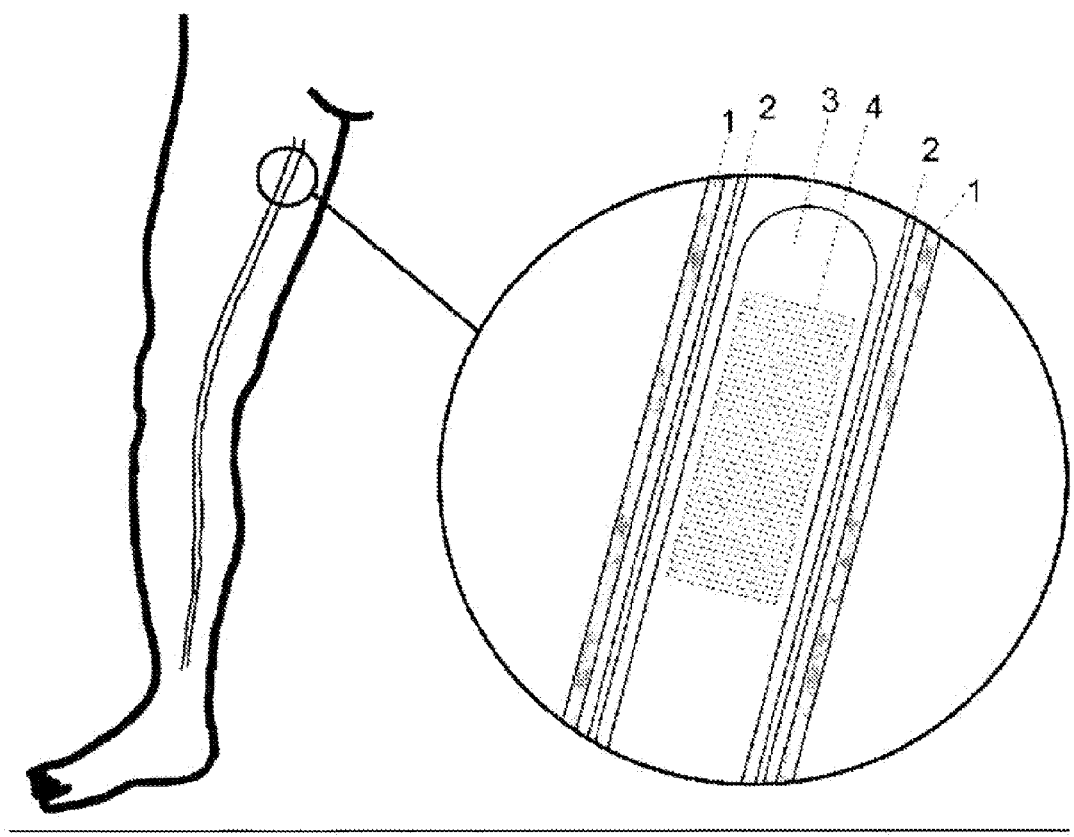
FIG. 1 shows the positioning of the catheter system (2) and the light applicator (3) with light-emitting area (4) in the blood vessel (1). The light emitting area may be a part of or an extension of an optic fibre.
Figure 2:
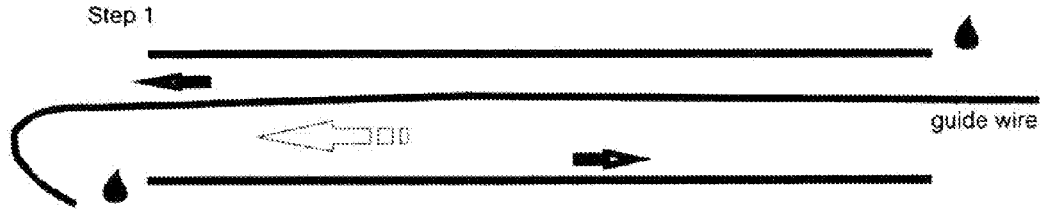
FIG. 2 shows schematically a possible introduction of the device of the present invention using a two step process ("principle a") employing the Seldinger technique. Upon puncture with an access needle, a guide wire is inserted into the vessel through the access needle. The guide wire guides the catheter, which is inserted starting with the (open) distal end along said guiding wire. Upon positioning the catheter, the guide wire is removed and the light applicator is inserted into the catheter and used to apply energy. The light applicator may be movable within the catheter and is capable of emitting light through the catheter, e.g. also through the open distal end yet especially through the sheath of the catheter in a cylindrical manner. Upon finalizing the treatment, the light applicator may be removed from the catheter. Finally. the catheter is removed from the vessel.
Figure 2:
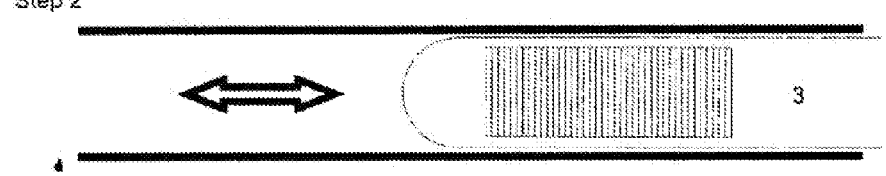
Figure 2:
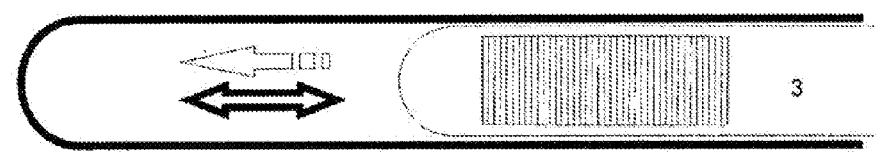
Figure 3:
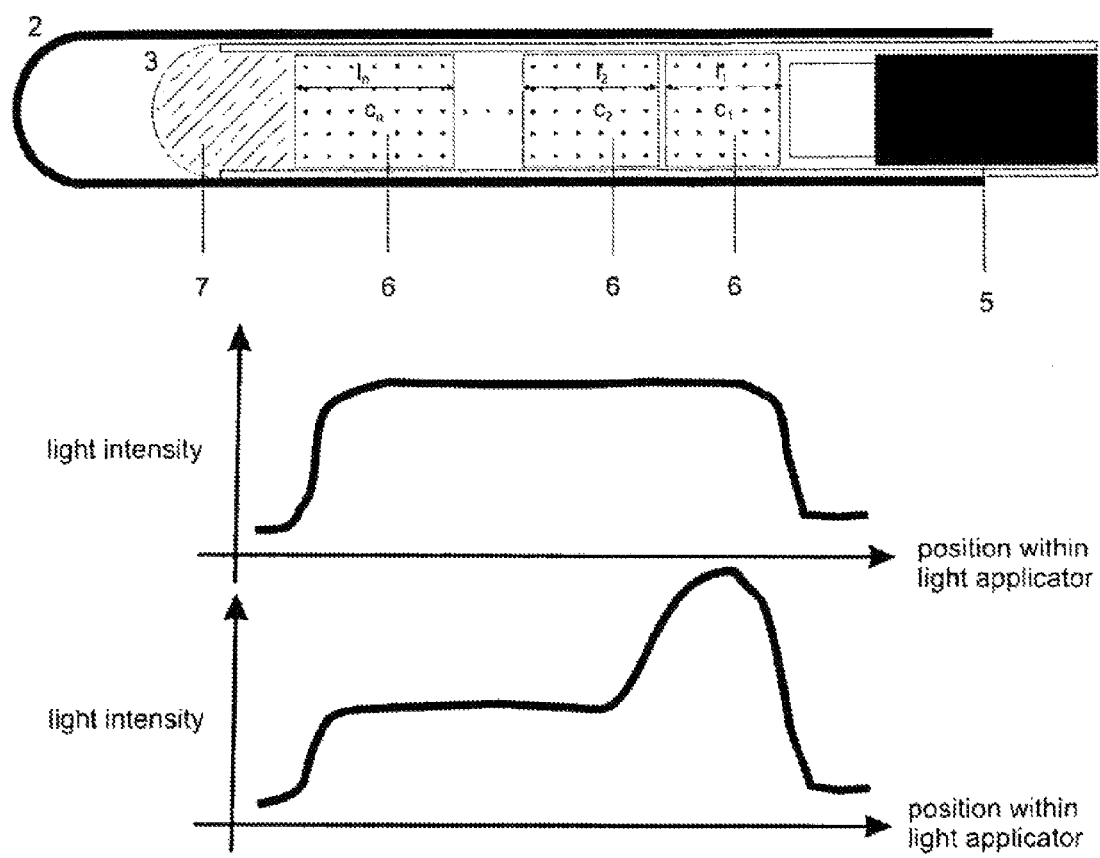

FIG. 3 shows exemplary radiation profiles of the light applicator in use. Here, the light applicator is a cylindrical diffuser based on a conventional optical fibre 5. The upper graph shows a homogeneous cylindrical radiation profile. The lower graph shows an inhomogeneous cylindrical radiation profile. The profiles can be created for example by the arrangement of different concentration of volume scattering layers ($c_1$ to $c_n$ in the Figure) as desired.

The figure shows different scatter layers $c_1$ to $c_n$, each comprising a medium with scattering particles 6) which may be used to set up the radiation profile by coupling out a distinct portion of light.

The device in FIG. 3 also shows an embodiment, which comprises a closure 7 of the light applicator. Here, e.g. an ultrasound or x-ray label may be placed within the applicator yet outside the light-emitting region for not being absorbing.

The invention claimed is:

1. A blood vessel treatment device, comprising:
 a light applicator; and
 a catheter, comprising a sheath, via which the light applicator is inserted into and guided within a blood vessel, wherein the sheath is flexible and non-expandable in the radial direction along an entire length of the sheath, wherein the catheter is open at a proximal end of the catheter, and wherein the catheter is closed at a distal portion of the catheter; and
 wherein the catheter and the light applicator are arranged and adapted such that, at any time during use, the light applicator does not make intraluminal contact with any vessel wall and the light applicator is capable of delivering light energy through a sheath of the catheter so as to emit light energy and cause damage to a vessel wall of the blood vessel, the damage resulting in a subsequent decrease in a diameter of the blood vessel,
 during use, the light applicator is movable within the catheter in consecutive segments or at a constant velocity of 1-5 mm/s, and
 during use, the light applicator may be placed repeatedly at the same position within the vessel without moving the catheter.

2. The device of claim 1, further comprising a light emitting unit, said light emitting unit being connected to the light applicator.

3. The device of claim 1, wherein the light energy is laser light energy of a wavelength in the range 500-2000 nm.

4. The device of claim 1, wherein the light applicator is placed within the sheath of the catheter.

5. The device of claim 1, wherein the light applicator is capable of delivering light energy to the blood vessel using the Seldinger Technique or a kind of Seldinger Technique.

6. The device of claim 1, wherein
 a diameter of the light applicator is between 0.1 and 2.5 mm,
 a length of a light emitting surface of the light applicator is between 3 to 70 mm, and
 a power density of the emitting surface of the light applicator is between 10 to 100 $W/cm^2$.

7. The device of claim 1, wherein the light applicator comprises a fiber optic line and cylindrical diffuser.

8. The device of claim 7, wherein
 the cylindrical diffuser emits light in an inhomogeneous profile such that more light energy is provided at a distal end than a non-distal end of the light applicator.

9. The device of claim 7, wherein the cylindrical diffuser emits light in a homogeneous profile over the surface of the cylindrical diffuser.

10. The device of claim 7, wherein
the entire sheath of the catheter comprises a tubular envelope of consistent diameter, and
a distal end of the catheter is closed by a closure, a diameter of the closure being substantially equivalent to the diameter of the sheath of the catheter.

11. The device of claim 1, wherein the light applicator emits light in a cylindrical radiation profile.

12. The device of claim 1, further comprising at least one of:
a contrast unit that captures images of the blood vessel to be treated;
a velocity control unit that controls a velocity at which the light applicator is moved within the catheter;
a temperature detecting unit that determines a temperature at a position where the blood vessel is to be damaged;
a coagulation detecting unit that determines coagulation at a position where the blood vessel is to be damaged;
an imaging unit that displays the data measured by at least one of the contrast unit, the velocity control unit, the temperature detecting unit, and the coagulation detecting unit; and
a closed loop unit that controls at least one of the parameters of light intensity, velocity, and segmentation of movement.

13. The device of claim 1, further comprising:
a velocity control unit that controls a velocity at which the light applicator is moved within the catheter; and
a temperature detecting unit that determines a temperature at a position where the blood vessel is to be damaged.

14. A kit, comprising:
a light applicator;
a catheter via which the light applicator is inserted into and guided within a blood vessel; and
an access needle;
wherein the catheter and the light applicator are arranged and adapted such that, at any time during use, the light applicator does not make intraluminal contact with any vessel wall and the light applicator is capable of delivering light energy through the catheter to emit light energy and cause damage to a vessel wall of the blood vessel, and
a sheath of the catheter is flexible and non-expandable in the radial direction along an entire length of the sheath that is at least partially optically transmissible to emit light energy from the light applicator, wherein the catheter is open at a proximal end of the catheter, and wherein the catheter is closed at a distal portion of the catheter.

15. The kit of claim 14, wherein the catheter comprises a single opening only, wherein the opining is at a proximal end of the catheter.

16. A blood vessel treatment device, comprising:
a light applicator; and
a catheter via which the light applicator is inserted into and guided within a blood vessel,
wherein the catheter and light applicator are arranged and adapted such that, at any time during use, the light applicator does not make intraluminal contact with any vessel wall and the light applicator is capable of delivering light energy through a sheath of the catheter so as to emit light energy and cause damage to a vessel wall of the blood vessel, the damage resulting in a subsequent decrease in a diameter of the blood vessel, and
the sheath of the catheter is flexible and non-expandable in the radial direction along an entire length of the sheath that is at least partially optically transmissible to emit light energy from the light applicator, wherein the catheter is open at a proximal end of the catheter, and wherein the catheter is closed at a distal portion of the catheter.

* * * * *